United States Patent
Zhou et al.

(10) Patent No.: US 8,692,018 B2
(45) Date of Patent: Apr. 8, 2014

(54) APPLICATION OF IRIDIUM COMPLEXES IN ASYMMETRIC CATALYTIC HYDROGENATION OF UNSATURATED CARBOXYLIC ACIDS

(75) Inventors: Qilin Zhou, Tianjin (CN); Shen Li, Tianjin (CN); Shoufei Zhu, Trianjin (CN); Canming Zhang, Tianjin (CN); Lixin Wang, Tianjin (CN)

(73) Assignee: Zheijiang Jiuzhou Pharmaceutical Co., Ltd. (CN)

( * ) Notice: Subject to any disclaimer, the term of this patent is extended or adjusted under 35 U.S.C. 154(b) by 501 days.

(21) Appl. No.: 12/989,620

(22) PCT Filed: Jan. 20, 2009

(86) PCT No.: PCT/CN2009/070231
§ 371 (c)(1),
(2), (4) Date: Oct. 25, 2010

(87) PCT Pub. No.: WO2009/129701
PCT Pub. Date: Oct. 29, 2009

(65) Prior Publication Data
US 2011/0092732 A1    Apr. 21, 2011

(30) Foreign Application Priority Data

Apr. 25, 2008 (CN) .......................... 2008 1 0052884

(51) Int. Cl.
*C07C 63/04* (2006.01)
(52) U.S. Cl.
USPC .......................................................... 562/493
(58) Field of Classification Search
CPC ...................................................... C07C 63/04
See application file for complete search history.

(56) References Cited

FOREIGN PATENT DOCUMENTS

CN          1884290 A     12/2006

OTHER PUBLICATIONS

Li et al, Journal of the American Chemical Society, Iridium-Catalyzed Enantioselective Hydrogenation of ___, _—Unsaturated Carboxylic Acids, 2008, 130, pp. 8584-8585 with supporting information.*
White et al, Basic Energy Sciences Advisory Committee Subpanel Workshop Report, Opportunities for Catalysis in the 21st Century, 2002, pp. 1-47.*
Li, Shen et al., Iridium-Catalyzed Enantioselective Hydrogenation of a,?—Unsaturated Carboxylic Acids, Journal of the American Chemical Society, Jun. 2008, vol. 130, No. 27, pp. 8584-8585.
Zhu, Shoufei et al., Well-Defined Chiral Spiro Iridium/Phosphine-Oxazoline Cationic Complexes for Highly Enantioselective Hydrogenation of Imines at Ambient Pressure, Journal of the American Chemical Society, 2006, vol. 128, No. 39, pp. 12886-12891.
Selvakumar, Kumaravel et al.; Catalytic and Structural Studies on Complexes of a Binaphthyl-Phosphino-Oxazoline Auxiliary: The Meta Dialkyl Effect on Enantioselectivity, Organometallics, 2000, vol. 19, No. 7, pp. 1299-1307.
Zhang, Zhanhui, Synthesis and Application of Chiral Priro Ligands in Asymmertric Catalysis, Chinese Journal of Organic Chemistry, 2005, vol. 25, No. 4, pp. 355-363.

* cited by examiner

*Primary Examiner* — Paul A Zucker
(74) *Attorney, Agent, or Firm* — Blue Filament Law PLLC; Avery N. Goldstein

(57) ABSTRACT

The present invention relates to a preparation method of carboxylic acids with optical activity, particularly, publishes that very useful chiral carboxylic acids can be obtained by the asymmetric catalytic hydrogenation of tri-substituted α,β-unsaturated carboxylic acids, with the complexes of the chiral phosphor nitrogen ligands and iridium used as the catalysts which show high activity and enantioselectivity (up to 99.8% ee), thus provides a more efficient method with higher enantioselectivity for asymmetric catalytic hydrogenation of chiral carboxylic acid-like compounds, and has important application value to asymmetric hydrogenation of chiral carboxylic acids.

7 Claims, No Drawings

APPLICATION OF IRIDIUM COMPLEXES IN ASYMMETRIC CATALYTIC HYDROGENATION OF UNSATURATED CARBOXYLIC ACIDS

CROSS-REFERENCE TO RELATED APPLICATIONS

This application is the U.S. national phase of PCT/CN2009/070231 filed Jan. 20, 2009, which claims priority of Chinese Patent Application No. 200810052884.X filed Apr. 25, 2008.

FIELD OF TECHNOLOGY

The present invention relates to a preparation method of carboxylic acids with optical activity, particularly, publishes the application of iridium complexes of chiral phosphor nitrogen ligands in asymmetric catalytic hydrogenation of tri-substituted α,β-unsaturated carboxylic acids for preparing chiral carboxylic acids. In the invention, very useful chiral carboxylic acids can be obtained by the asymmetric catalytic hydrogenation of tri-substituted α,β-unsaturated carboxylic acids, with the complexes of the chiral phosphor nitrogen ligands and iridium used as the catalysts which show high activity and enantioselectivity (up to 99.8% ee). This is one of the most efficient methods for synthesizing carboxylic acids with optical activity by the asymmetric catalytic hydrogenation.

DESCRIPTION OF RELATED ARTS

In organic synthesis, the chiral carboxylic acids are important components of a lot of natural products with biological activity and drug molecules, so the development of the synthesis methods of optically pure carboxylic acid-like compounds is one of the hot research fields in the current academia and industry (Lednicer, D.; Mitscher, L. A. *The Organic Chemistry of Drug Synthesis* 1977 and 1980, Wiley: New York, Vols. 1 and 2). Among many methods for synthesizing unsaturated carboxylic acids, the asymmetric catalytic hydrogenation of α,β-unsaturated carboxylic acids attracted great interest from researchers for its atoms are highly economic and it is environmental friendly (Jacobsen, E. N.; Pfaltz, A.; Yamamoto, H. *Comprehensive Asymmetric Catalysis*, Springer: Berlin, 1999, Vols. I.; Tang, W.; Zhang, X. *Chem. Rev.* 2003, 103, 3029). In 1987, Noyori achieved the homogeneous asymmetric catalytic hydrogenation of α,β-unsaturated carboxylic acid—tiglic acid for the first time with the ruthenium acetate complex of BINAP as the catalyst, and obtained the ee value of 91%, and also prepared (S)-Naproxen with the same catalyst, and obtained the ee value of 97% (Ohta, T.; Takaya, H.; Kitamura, M.; Nagai, K.; Noyori, R. *J. Org. Chem.* 1987, 52, 3176). Since then, people have developed several chiral ruthenium and rhodium complex catalysts, they achieved very good catalytic effects in the catalytic asymmetric hydrogenation of unsaturated carboxylic acids, and there are many examples of successful industrialization (Boogers J. A. F.; Felfer, U.; Kotthaus, M.; Lefort, L.; Steinbauer, G.; de Vries, A. H. M.; de Vries, J. G. *Org. Proc. Res. Dev.* 2007, 11, 585). However, due to the specificity of catalytic hydrogenation reaction, each catalyst can be effective only to one or a few kinds of substrates, so far there are still many substrates that can not be catalyzed well; and, most of known chiral catalysts still have various defects, which appear mainly to be higher amount of catalysts, rigorous reaction conditions, too long reaction time and so on. Therefore, there is a need to find more effective chiral catalysts, to achieve hydrogenation of α,β-unsaturated carboxylic acids with high enantioselectivity.

In addition to ruthenium and rhodium complexes, the chiral catalysts formed by the transition metal iridium and chiral ligands are also used broadly in asymmetric catalytic hydrogenation, particularly the asymmetric hydrogenation of the non-functional groups olefin and imine, and results better than other transition metal catalysts can be obtained ((Blaser, H.-U. *Adv. Synth. Catal.* 2002, 344, 17; Zhou, Y.-G. *Acc. Chem. Res.* 2007, 40, 1357; Roseblade, S. J.; Pfaltz, A. *Acc. Chem. Res.* 2007, 40, 1402). However, so far there is only one report about the iridium complex for asymmetric hydrogenation of unsaturated carboxylic acids, that is, Matteoli et. al. catalyzed the asymmetric hydrogenation of a di-substituted α,β-unsaturated carboxylic acid-α-phenylethyl acrylic acid with a chiral iridium catalyst, but that catalyst only showed moderate reactivity and enantioselectivity (Scrivanti, A.; Bova, S.; Ciappa, A.; Matteoli, U. *Tetrahedron Lett.* 2006, 47, 9261). Therefore, the development of novel iridium complex catalysts to achieve high efficient asymmetric hydrogenation of α,β-unsaturated carboxylic acids has important research and application values.

SUMMARY OF THE INVENTION

Aspects of the present invention generally pertain to a preparation method of chiral carboxylic acids by using an iridium complex of a chiral phosphor nitrogen ligand in asymmetric catalytic hydrogenation of tri-substituted α,β-unsaturated carboxylic acids, which is a successful application of iridium complex catalysts in asymmetric catalytic hydrogenation of tri-substituted α,β-unsaturated carboxylic acids, thus provides a more efficient method with higher enantioselectivity for asymmetric catalytic hydrogenation of chiral carboxylic acid-like compounds.

The preparation method of chiral carboxylic acids by using the iridium complex of the chiral phosphor nitrogen ligand to catalyze asymmetric hydrogenation of tri-substituted α,β-unsaturated carboxylic acids provided by the present invention is that the asymmetric catalytic hydrogenation of the tri-substituted α,β-unsaturated carboxylic acids is carried out with the presence of an additive and the chiral iridium complex of the chiral phosphor nitrogen ligand to obtain chiral carboxylic acids having certain optical purity.

The preparation method of chiral carboxylic acids of the present invention, characterized in that it is carried out by the following catalytic hydrogenation reaction process:

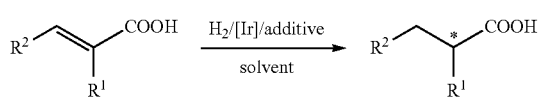

wherein: [Ir] is the iridium complex catalyst of the chiral phosphor nitrogen ligand; $R^1$, $R^2$ are halogen, hydroxyl, $C_1$-$C_8$ alkyl, halogenated alkyl, $C_1$-$C_8$ alkoxy, phenoxy, $C_1$-$C_8$ alkyl-substituted phenoxy, hydroxyl-substituted phenoxy, $C_1$-$C_8$ alkoxy-substituted phenoxy, $C_1$-$C_8$ acyloxy-substituted phenoxy, halogenated phenoxy, amino-substituted phenoxy, ($C_1$-$C_8$ acyl)amino-substituted phenoxy, di ($C_1$-$C_8$ alkyl)amino-substituted phenoxy, $C_1$-$C_8$ acyl-substituted phenoxy, $C_2$-$C_8$ esteryl-substituted phenoxy, naphthyloxy, furyloxy, thienyloxy, benzyloxy, $C_2$-$C_8$ acyloxy, $C_1$-$C_8$ acyl, $C_2$-$C_8$ esteryl, ($C_1$-$C_8$ acyl)amino, di ($C_1$-$C_8$ alkyl)amino, phenyl, $C_1$-$C_8$ alkyl-substituted phenyl, hydroxyl-substituted phenyl, $C_1$-$C_8$ alkoxy-substituted phenyl, $C_2$-$C_8$ acyloxy-substituted phenyl, halogenated phenyl, amino-substituted phenyl, ($C_1$-$C_8$ acyl)amino-substituted phenyl, di ($C_1$-$C_8$ alkyl)amino-substituted phenyl, $C_1$-$C_8$ acyl-substituted phenyl, $C_2$-$C_8$ esteryl-substituted phenyl, naphthyl, furyl, thienyl, respectively; $R^1$ and $R^2$ can be same or different; the position marked by the asterisk is the chiral center.

The preparation method of chiral carboxylic acids of the present invention is achieved with the iridium complex catalyst of the chiral phosphor nitrogen ligand has the following structural formula:

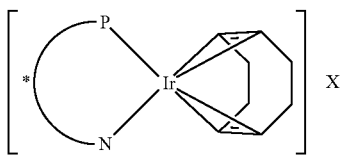

wherein:

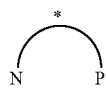

is the chiral phosphor nitrogen ligand;

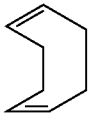

is cyclooctadiene; n=0-3; $R^1$, $R^2$, $R^3$, $R^4$, $R^5$, $R^6$, $R^7$ are defined as the compound (I); X is halogen, $C_1$-$C_8$ carboxylate radical, sulfate radical, tetra (3,5-bis trifluoromethylphenyl) borate radical, tetra (pentafluorophenyl) borate radical, tetra (perfluoro-tert-butoxy) aluminum ion, tetra (hexafluoroisopropoxy) aluminum ion, hexafluoro phosphate ion, hexafluoro antimonlate ion, tetrafluoro borate ion or trifluoro methanesulfonate ion; cyclooctadiene ligand can be substituted by ethylene or norbornadiene.

The chiral phosphor nitrogen ligand contained in the above-mentioned iridium complex catalyst of the chiral phosphor nitrogen ligand has the following structural formula:

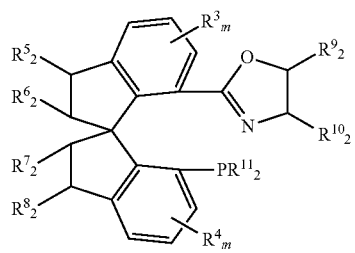

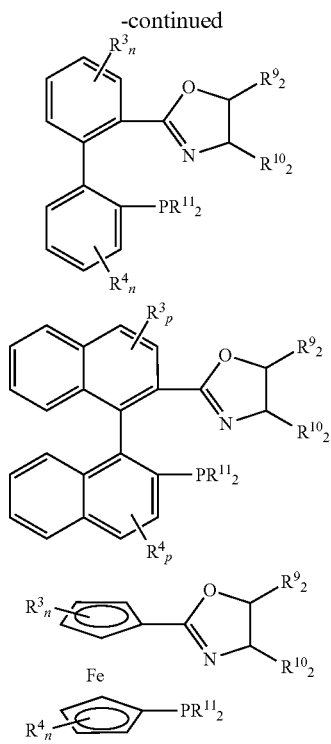

wherein: m=0-3, n=0-4, p=0-6; $R^3$, $R^4$ are H, $C_1$-$C_8$ alkyl, halogenated alkyl, $C_1$-$C_8$ alkoxy, $C_2$-$C_8$ acyloxy, $C_1$-$C_8$ acyl, $C_2$-$C_8$ esteryl, ($C_1$-$C_8$ acyl)amino, di ($C_1$-$C_8$ alkyl)amino, halogen, phenyl, $C_1$-$C_8$ alkyl-substituted phenyl, hydroxyl-substituted phenyl, $C_1$-$C_8$ alkoxy-substituted phenyl, $C_2$-$C_8$ acyloxy-substituted phenyl, halogenated phenyl, amino-substituted phenyl, ($C_1$-$C_8$ acyl)amino-substituted phenyl, di ($C_1$-$C_8$ alkyl)amino-substituted phenyl, $C_1$-$C_8$ acyl-substituted phenyl, $C_2$-$C_8$ esteryl-substituted phenyl, naphthyl, furyl, thienyl, respectively or combined alicyclic or aromatic ring when m, n, p≥2; $R^3$ and $R^4$ can be same or different;

$R^5$, $R^6$, $R^7$, $R^8$ are H, $C_1$-$C_8$ alkyl, halogenated alkyl, $C_1$-$C_8$ alkoxy, $C_2$-$C_8$ acyloxy, $C_1$-$C_8$ acyl, $C_2$-$C_8$ esteryl, ($C_1$-$C_8$ acyl)amino, di ($C_1$-$C_8$ alkyl)amino, halogen, phenyl, $C_1$-$C_8$ alkyl-substituted phenyl, hydroxyl-substituted phenyl, $C_1$-$C_8$ alkoxy-substituted phenyl, $C_2$-$C_8$ acyloxy-substituted phenyl, halogenated phenyl, amino-substituted phenyl, ($C_1$-$C_8$ acyl)amino-substituted phenyl, di ($C_1$-$C_8$ alkyl)amino-substituted phenyl, $C_1$-$C_8$ acyl-substituted phenyl, $C_2$-$C_8$ esteryl-substituted phenyl, naphthyl, furyl, thienyl, respectively or $R^5$~$R^6$, $R^7$~$R^8$ are combined alicyclic or aromatic ring; $R^5$, $R^6$, $R^7$, $R^8$ can be same or different;

$R^9$, $R^{10}$ are H, $C_1$-$C_8$ alkyl, halogenated alkyl, $C_1$-$C_8$ alkoxy, $C_2$-$C_8$ acyloxy, $C_1$-$C_8$ acyl, $C_2$-$C_8$ esteryl, ($C_1$-$C_8$ acyl)amino, di ($C_1$-$C_8$ alkyl)amino, halogen, benzyl, phenyl, $C_1$-$C_8$ alkyl-substituted phenyl, hydroxyl-substituted phenyl, $C_1$-$C_8$ alkoxy-substituted phenyl, $C_2$-$C_8$ acyloxy-substituted phenyl, halogenated phenyl, amino-substituted phenyl, ($C_1$-$C_8$ acyl)amino-substituted phenyl, di ($C_1$-$C_8$ alkyl)amino-substituted phenyl, $C_1$-$C_8$ acyl-substituted phenyl, $C_2$-$C_8$ esteryl-substituted phenyl, naphthyl, furyl, thienyl, respectively or $R^9$~$R^{10}$ are combined alicyclic or aromatic ring; $R^9$ and $R^{10}$ can be same or different;

$R^{11}$ is $C_1$-$C_8$ alkyl, phenyl, $C_1$-$C_8$ alkyl-substituted phenyl, hydroxyl-substituted phenyl, sulfo-substituted phenyl, $C_1$-$C_8$ alkoxy-substituted phenyl, $C_2$-$C_8$ acyloxy-substituted phenyl, halogenated phenyl, amino-substituted phenyl, ($C_1$~$C_8$ acyl)amino-substituted phenyl, di (C$_1$-C$_8$ alkyl)amino-substituted phenyl, C$_1$-C$_8$ acyl-substituted phenyl, C$_2$-C$_8$ esteryl-substituted phenyl, naphthyl, furyl, thienyl;

the C$_1$~C$_8$ alkyl is methyl, ethyl, n-propyl, isopropyl, cyclopropyl, n-butyl, isobutyl, sec-butyl, tert-butyl, cyclobutyl, pentyl, isoamyl, neopentyl, sec-pentyl, tert pentyl, cyclopentyl, n-hexyl, isohexyl, neohexyl, sec-hexyl, tert-hexyl, cyclohexyl, n-heptyl, isoheptyl, neoheptyl, sec-heptyl, tert-heptyl, cycloheptyl, n-octyl, isooctyl, neooctyl, sec-octyl, tert-octyl or cyclooctyl;

the C$_1$-C$_8$ alkoxy is methoxy, ethoxy, n-propoxy, isopropoxy, cyclopropoxy, n-butoxy, isobutoxy, sec-butoxy, tert-butoxy, cyclobutoxy, n-pentyloxy, isopentyloxy, neopentyloxy, sec-pentyloxy, tert-pentyloxy, cyclopentyloxy, n-hexyloxy, isohexyloxy, neohexyloxy, sec-hexyloxy, tert-hexyloxy, cyclohexyloxy, n-heptyloxy, isoheptyloxy, neoheptyloxy, sec-heptyloxy, tert-heptyloxy, cycloheptyloxy, n-octyloxy, iso-octyloxy, neooctyloxy, sec-octyloxy, tert-octyloxy, cyclooctyloxy;

the C$_1$-C$_8$ acyl is formoxyl, acetyl, propionyl, n-butyryl, isobutyryl, n-valeryl, isovaleryl, sec-valeryl, neovaleryl, n-hexanoyl, isohexanoyl, neohexanoyl, sec-hexanoyl, n-heptanoyl, isoheptanoyl, neoheptanoyl, sec-heptanoyl, n-octanoyl, isooctanoyl, neooctanoyl, sec-octanoyl, 1-cyclopropyl formoxyl, 1-cyclobutyl formoxyl, 1-cyclopentyl formoxyl, 1-cyclohexyl formoxyl, 1-cycloheptyl formoxyl;

the C$_2$-C$_8$ acyloxy is acetoxyl, propionyloxy, n-butyryloxy, isobutyryloxy, n-valeryloxy, isovaleryloxy sec-valeryloxy, neovaleryloxy, n-hexanoyloxy, isohexanoyloxy, neohexanoyloxy, sec-hexanoyloxy, n-heptanoyloxy, isoheptanoyloxy, neoheptanoyloxy, sec-heptanoyloxy, n-octanoyloxy, isooctanoyloxy, neooctanoyloxy, sec-octanoyloxy, 1-cyclopropyl acetoxyl, 1-cyclobutyl acetoxyl, 1-cyclopentyl acetoxyl, 1-cyclohexyl acetoxyl, 1-cycloheptyl acetoxyl;

the C$_2$-C$_8$ esteryl is methoxycarbonyl, ethoxycarbonyl, propoxycarbonyl, isopropoxycarbonyl, butoxycarbonyl, isobutoxycarbonyl, n-pentyloxycarbonyl, isopentyloxycarbonyl, neopentyloxycarbonyl, sec-pentyloxycarbonyl, tert-pentyloxycarbonyl, cyclopentyloxycarbonyl, n-hexyloxycarbonyl, isohexyloxycarbonyl, neohexyloxycarbonyl, sec-hexyloxycarbonyl, tert-hexyloxycarbonyl, cyclohexyloxycarbonyl, n-heptyloxycarbonyl, isoheptyloxycarbonyl, neoheptyloxycarbonyl, sec-heptyloxycarbonyl, tert-heptyloxycarbonyl, cycloheptyloxycarbonyl;

the halogenated alkyl is a halogenated alkyl containing fluoride, chlorine, bromine or iodine.

The preparation method of chiral carboxylic acids of the present invention is that: under the protection of argon or nitrogen, the catalyst and the substrate are added into the inner tube of the reactor, then the additive and the solvent are added, the reactor is sealed and the air in the reactor is replaced carefully with hydrogen for 3 to 5 times, after the reactor is filled with hydrogen to the desired pressure, the mixture is stirred to the end;

The solvent used is ethyl acetate or C$_1$-C$_6$ alcohol; the amount of the catalyst is 0.001-1 mol %; the concentration of the substrate is 0.001-10.0 M; the additive is one or several of iodine, isopropylamine, tert-butylamine, dimethylamine, diethyl amine, diisopropylamine, diisopropyl ethylamine, trimethylamine, triethylamine, 1,8-diazabicyclo[5,4,0]undec-7-ene (DBU), 1,4-diazabicyclo[2,2,2]octane (DABCO), sodium hydride, sodium hydroxide, sodium carbonate, sodium bicarbonate, sodium tert-butyl alcohol, potassium hydroxide, potassium carbonate, potassium bicarbonate, potassium tert-butyl alcohol, cesium hydroxide, cesium carbonate; the reaction temperature is 0-100° C.; the hydrogen pressure, is 0.1-10 Mpa; the tri-substituted α,β-unsaturated carboxylic acid is stirred in the reactor to react for 0.5-0.48 h.

The present invention provides a successful application of iridium complex catalysts of chiral phosphor nitrogen ligands in asymmetric catalytic hydrogenation of tri-substituted α,β-unsaturated carboxylic acids. Very useful chiral carboxylic acids can be obtained by the asymmetric catalytic hydrogenation of tri-substituted α,β-unsaturated carboxylic acids, with the complexes of the chiral phosphor nitrogen ligands and iridium used as the catalysts which show high activity and enantioselectivity (up to 99.8% ee), thus the present invention provides a more efficient method with higher enantioselectivity for asymmetric catalytic hydrogenation of chiral carboxylic acid-like compounds, and has important application value to asymmetric hydrogenation of chiral carboxylic acids.

DETAILED DESCRIPTION OF THE PREFERRED EMBODIMENT

The following embodiments will facilitate to further understand the present invention, but do not limit the contents of the present invention. The preparation method of the present invention can be shown further with the representative compounds as follows:

General explanation:

The following abbreviations are used in the embodiments, and their meanings are as follows:

Me is methyl, $^n$Pr is n-propyl, $^i$Pr is isopropyl, $^i$Bu is isobutyl, $^t$Bu is tert-butyl, Ph is phenyl, Bn is benzyl, An is p-methoxyphenyl, Xyl is 3,5-dimethylphenyl, DMM is 3,5-dimethyl-4-methoxyphenyl, DTB is 3,5-di-tert-butyl-phenyl, BARF- is tetra (3,5-bis trifluoromethylphenyl) borate radical; PF$_6^-$ is hexafluoro phosphate ion, Naphthyl is naphthyl, Furan-2-yl is 2-furyl; NMR is nuclear magnetic resonance, the chiral SFC is a supercritical fluid chromatography equipped with a chiral column, the chiral HPLC is a high pressure liquid chromatography equipped with a chiral chromatographic column; the ee value is the excess value of enantiomer.

The solvents used are purified and dried with the standard operation before use; the reagents used are commercially available or synthesized according to the existing literature methods and purified before use.

Embodiment 1

Asymmetric Catalytic Hydrogenation of α-methyl Cinnamic Acid

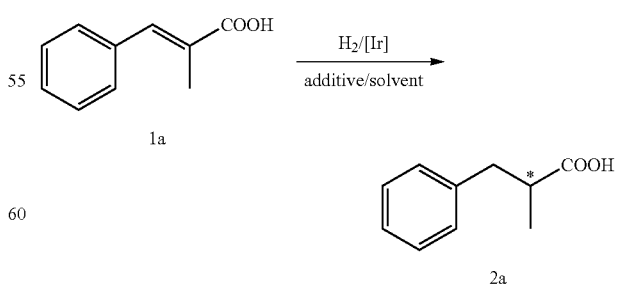

In the glove box, the catalyst (0.00125 mmol) and α-methyl cinnamic acid 1a (81 mg, 0.5 mmol) are weighted in the reaction inner tube with stirring bar, then the reaction inner tube is sealed for use. When the reaction inner tube is took out, the additive and the solvent are added, then the inner tube is placed into the hydrogenation reactor, the mixture is stirred under the hydrogen pressure of 0.6~10 Mpa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 2a is obtained. The conversion rate is analyzed through $^1$H NMR, after it is converted to amide, its ee value is analyzed through the chiral HPLC analysis. The experimental results obtained are shown in Table 1:

TABLE 1 the experimental results of asymmetric catalytic hydrogenation of α-methyl cinnamic acid 1a

| | Catalyst | Hydrogen pressure | Additive | Solvent | Temperature | Conversion rate | ee value |
|---|---|---|---|---|---|---|---|
| 1 | [structure with BARF⁻] | 0.6 MPa | Non | methanol | room temperature | 15% | 82% |
| 2 | [structure with BARF⁻] | 0.6 MPa | Non | methanol | room temperature | 0 | |
| 3 | [structure with BARF⁻] | 0.6 MPa | Non | methanol | room temperature | 17% | 80% |
| 4 | [structure with PF₆⁻] | 0.6 MPa | Non | methanol | room temperature | 18% | 65% |
| 5 | [structure with BARF⁻] | 0.6 MPa | Non | methanol | room temperature | 61% | 53% |

TABLE 1-continued the experimental results of asymmetric catalytic hydrogenation of α-methyl cinnamic acid 1a

| | Catalyst | | Hydrogen pressure | Additive | Solvent | Temperature | Conversion rate | ee value |
|---|---|---|---|---|---|---|---|---|
| 6 | 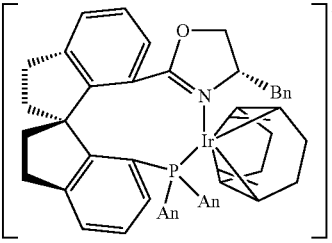 | BARF⁻ | 0.6 MPa | Non | methanol | room temperature | 16% | 85% |
| 7 | 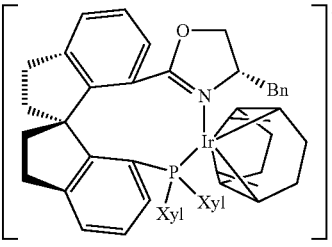 | BARF⁻ | 0.6 MPa | Non | methanol | room temperature | 30% | 76% |
| 8 | 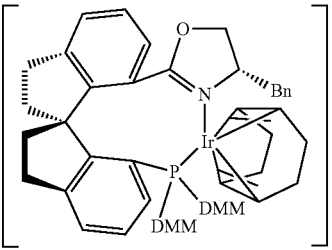 | BARF⁻ | 0.6 MPa | Non | methanol | room temperature | 25% | 72% |
| 9 | 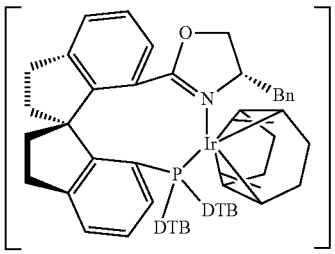 | BARF⁻ | 0.6 MPa | Non | methanol | room temperature | 58% | >99% |
| 10 | 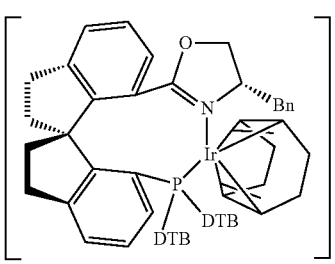 | BARF⁻ | 2 MPa | Non | methanol | room temperature | 62% | 98% |

TABLE 1-continued the experimental results of asymmetric catalytic hydrogenation of α-methyl cinnamic acid 1a

| | Catalyst | Hydrogen pressure | Additive | Solvent | Temperature | Conversion rate | ee value |
|---|---|---|---|---|---|---|---|
| 11 | 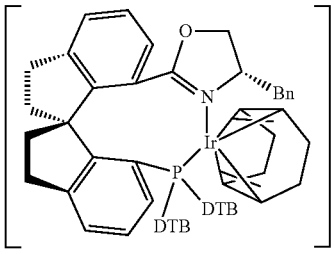 BARF⁻ | 5 MPa | Non | methanol | room temperature | 63% | 96% |
| 12 | 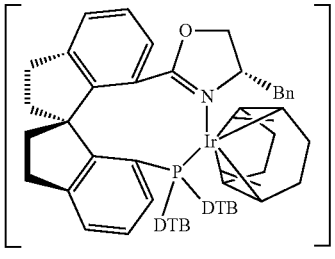 BARF⁻ | 10 MPa | Non | methanol | room temperature | 65% | 91% |
| 13 | 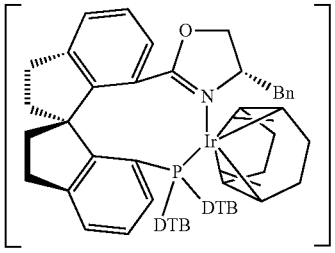 BARF⁻ | 0.6 MPa | Non | ethyl acetate | room temperature | 45% | 86% |
| 14 | 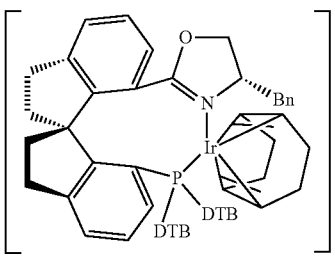 BARF⁻ | 0.6 MPa | Non | dichloromethane | room temperature | 0 | |
| 15 | 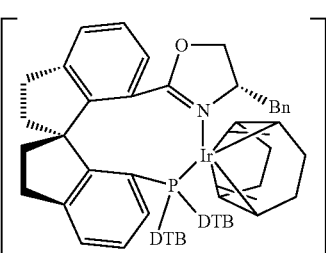 BARF⁻ | 0.6 MPa | Non | diethyl ether | room temperature | 0 | |

TABLE 1-continued the experimental results of asymmetric catalytic hydrogenation of α-methyl cinnamic acid 1a

| | Catalyst | Hydrogen pressure | Additive | Solvent | Temperature | Conversion rate | ee value |
|---|---|---|---|---|---|---|---|
| 16 | 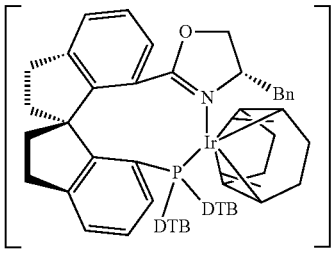 | 0.6 MPa | Non | tetrahydrofuran | room temperature | 0 | |
| 17 | 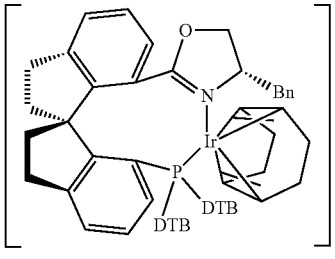 | 0.6 MPa | Non | methylbenzene | Room temperature | 0 | |
| 18 | 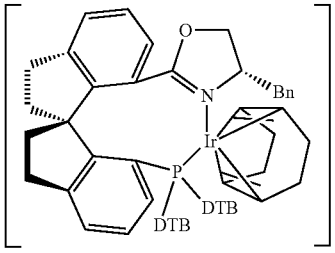 | 0.6 MPa | Non | methanol | 50° C. | 85% | 94% |
| 19 | 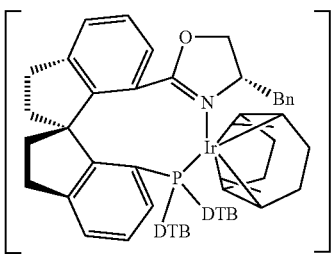 | 0.6 MPa | iodine | methanol | room temperature | 0 | |
| 20 | 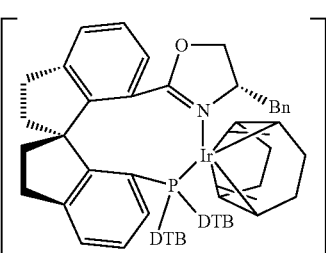 | 0.6 MPa | NaBARF3H$_2$O | methanol | room temperature | 54% | 99% |

TABLE 1-continued the experimental results of asymmetric catalytic hydrogenation of α-methyl cinnamic acid 1a

| | Catalyst | Hydrogen pressure | Additive | Solvent | Temperature | Conversion rate | ee value |
|---|---|---|---|---|---|---|---|
| 21 | 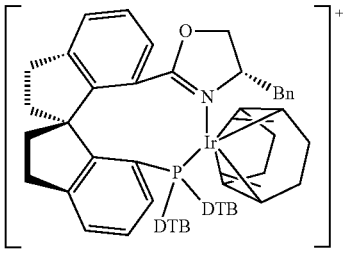 | 0.6 MPa | Triethylamine (0.05 mmol) | methanol | 室温 room temperature | 60% | >99% |
| 22 | 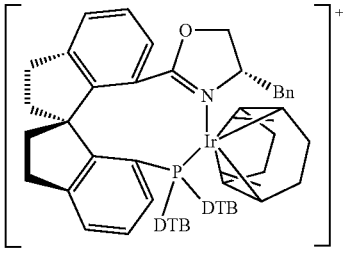 | 0.6 MPa | Triethylamine (0.1 mmol) | methanol | room temperature | 75% | >99% |
| 23 | 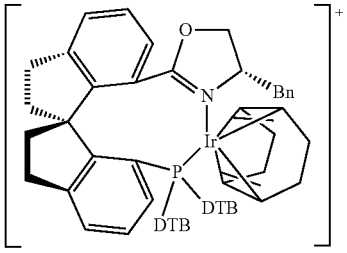 | 0.6 MPa | Triethylamine (0.25 mmol) | methanol | room temperature | 100% | >99% |
| 24 | 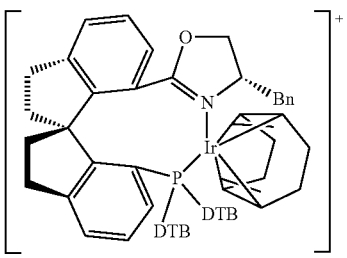 | 0.6 MPa | Triethylamine (0.5 mmol) | methanol | room temperature | 100% | >99% |
| 25 | 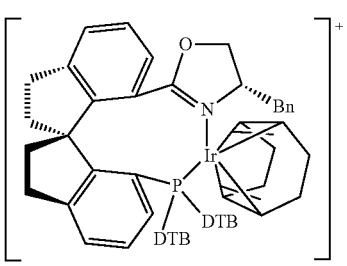 | 0.6 MPa | Triethylamine (0.25 mmol) | ethanol | room temperature | 95% | >99% |

TABLE 1-continued the experimental results of asymmetric catalytic hydrogenation of α-methyl cinnamic acid 1a

| | Catalyst | | Hydrogen pressure | Additive | Solvent | Temperature | Conversion rate | ee value |
|---|---|---|---|---|---|---|---|---|
| 26 | 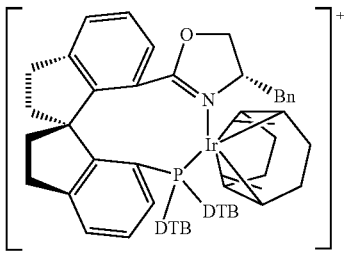 | BARF⁻ | 0.6 MPa | Triethylamine (0.25 mmol) | isopropanol | room temperature | 100% | 99% |
| 27 | 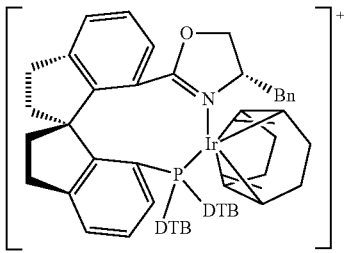 | BARF⁻ | 0.1 MPa | Triethylamine (0.25 mmol) | methanol | room temperature | 100% | >99% |
| 28 | 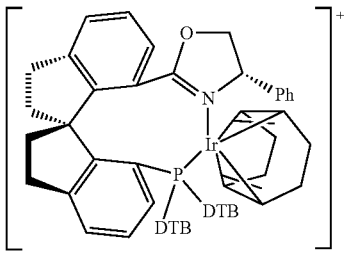 | BARF⁻ | 0.6 MPa | Triethylamine (0.25 mmol) | methanol | room temperature | 100% | 96% |
| 29 | 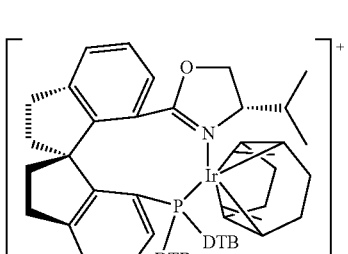 | BARF⁻ | 0.6 MPa | Triethylamine (0.25 mmol) | methanol | room temperature | 100% | >99% |
| 30 | 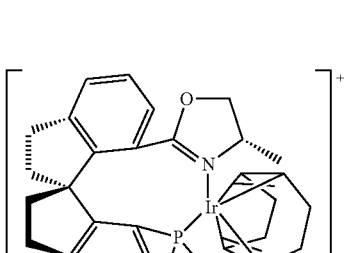 | BARF⁻ | 0.6 MPa | Triethylamine (0.25 mmol) | methanol | room temperature | 100% | >99% |

TABLE 1-continued the experimental results of asymmetric catalytic hydrogenation of α-methyl cinnamic acid 1a

| | Catalyst | Hydrogen pressure | Additive | Solvent | Temperature | Conversion rate | ee value |
|---|---|---|---|---|---|---|---|
| 31 | 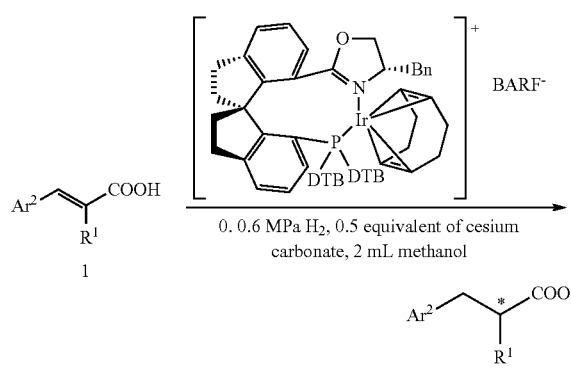 | 0.6 MPa | Triethylamine (0.25 mmol) | methanol | room temperature | 100% | >99% |

Embodiment 2

Asymmetric Catalytic Hydrogenation of α-methyl Cinnamic Acid Derivatives

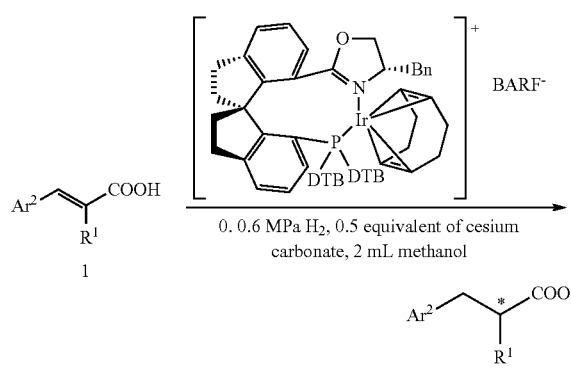

In the glove box, the catalyst

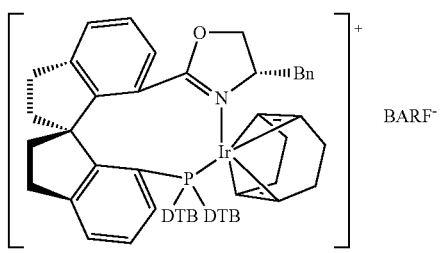

(2.4 mg, 0.00125 mmol) and the substrate 1 (0.5 mmol) are weighted in the reaction inner tube with stirring bar, then the reaction inner tube is sealed for use. When the reaction inner tube is took out, triethylamine (35 μL, 0.25 mmol) and anhydrous methanol (2 mL) are added with a syringe, then the inner tube is placed into the hydrogenation reactor, the mixture is stirred under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 2 is obtained. The conversion rate is analyzed through $^1$H NMR, after it is converted to amide, its ee value is analyzed through the chiral HPLC or SFC analysis. The experimental results obtained are shown in Table 2:

TABLE 2 the experimental results of asymmetric catalytic hydrogenation of α-substituted cinnamic acids

| | $R^1$ | $Ar^2$ | Conversion rate | Yield | ee value |
|---|---|---|---|---|---|
| 1 | Me | Ph | 100% | 99% | >99% |
| 2 | Me | 2-MeC$_6$H$_4$ | 100% | 97% | 99% |
| 3 | Me | 3-MeC$_6$H$_4$ | 100% | 98% | 99% |
| 4 | Me | 4-MeC$_6$H$_4$ | 100% | 98% | >99% |
| 5 | Me | 2-MeOC$_6$H$_4$ | 100% | 98% | 99% |
| 6 | Me | 3-MeOC$_6$H$_4$ | 100% | 99% | 98% |
| 7 | Me | 4-MeOC$_6$H$_4$ | 100% | 97% | 99% |
| 8 | Me | 2-ClC$_6$H$_4$ | 100% | 97% | 96% |
| 9 | Me | 3-ClC$_6$H$_4$ | 100% | 98% | 99% |
| 10 | Me | 4-ClC$_6$H$_4$ | 100% | 97% | 98% |
| 11 | Me | 3-BrC$_6$H$_4$ | 100% | 97% | 99% |
| 12 | Me | 4-BrC$_6$H$_4$ | 100% | 97% | 98% |
| 13 | Me | 4-CF$_3$C$_6$H$_4$ | 100% | 98% | 97% |
| 14 | Me | 2-Naphthyl | 100% | 96% | 99% |
| 15 | Me | Furan-2-yl | 100% | 98% | 98% |
| 16 | $^i$Pr | Ph | 100% | 97% | 99% |

Embodiment 3

Asymmetric Catalytic Hydrogenation of Tiglic Acid

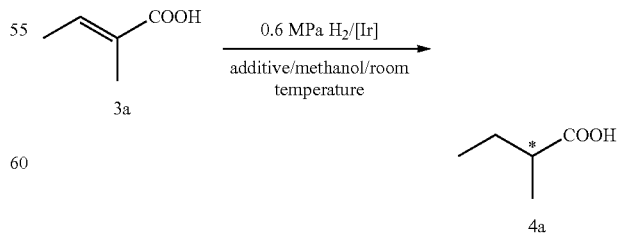

In the glove box, the catalyst (0.00125 mmol) and tiglic acid 3a (50 mg, 0.5 mmol) are weighted in the reaction inner tube with stirring bar, then the reaction inner tube is sealed for use. When the reaction inner tube is took out, the additive and the solvent (2 mL) are added, then the inner tube is placed into the hydrogenation reactor, the mixture is stirred under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 4a is obtained. The conversion rate is analyzed through $^1$H NMR, after it is converted to amide, its ee value is analyzed through the chiral HPLC or SFC analysis. The experimental results obtained are shown in Table 3:

TABLE 3 the experimental results of asymmetric catalytic hydrogenation of tiglic acid

| | Catalyst | Additive | Solvent | Conversion rate | ee value |
|---|---|---|---|---|---|
| 1 | [structure with Bn] BARF$^-$ | triethylamine (0.25 mmol) | methanol | 95% | 97% |
| 2 | [structure with Ph] BARF$^-$ | triethylamine (0.25 mmol) | methanol | 100% | 94% |
| 3 | [structure with iPr] BARF$^-$ | triethylamine (0.25 mmol) | methanol | 90% | 98% |
| 4 | [structure] BARF$^-$ | triethylamine (0.25 mmol) | methanol | 95% | 97% |
| 5 | [structure with iPr] BARF$^-$ | pyridine (0.25 mmol) | methanol | 0 | — |

TABLE 3-continued the experimental results of asymmetric catalytic hydrogenation of tiglic acid

| | Catalyst | Additive | Solvent | Conversion rate | ee value |
|---|---|---|---|---|---|
| 6 | 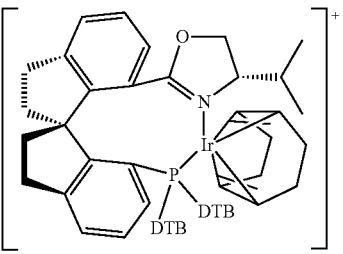 BARF⁻ | diisopropyl ethylamine (0.25 mmol) | methanol | 95% | 99% |
| 7 | 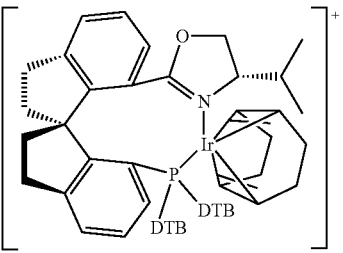 BARF⁻ | diisopropyl amine (0.25 mmol) | methanol | 95% | 99% |
| 8 | 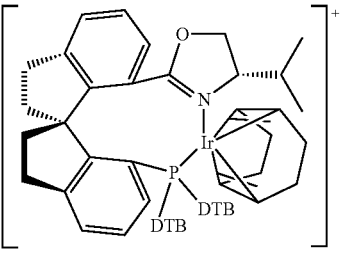 BARF⁻ | potassium hydroxide (025 mmol) | methanol | 95% | 98% |
| 9 | 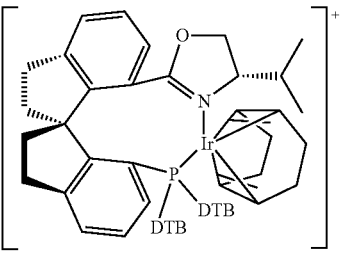 BARF⁻ | potassium acetate (0.25 mmol) | methanol | 80% | 96% |
| 10 | 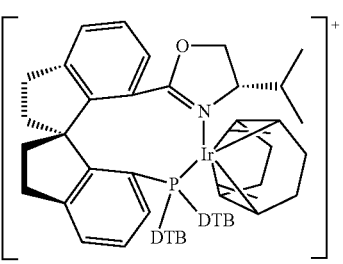 BARF⁻ | potassium bicarbonate (0.25 mmol) | methanol | 85% | 98% |

TABLE 3-continued
the experimental results of asymmetric catalytic hydrogenation of tiglic acid
| | Catalyst | Additive | Solvent | Conversion rate | ee value |
|---|---|---|---|---|---|
| 11 | 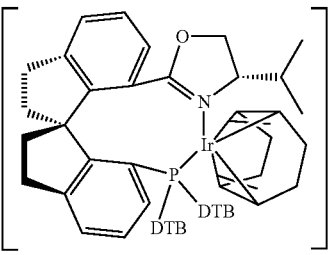 | potassium carbonate (0.25 mmol) | methanol | 100% | 99% |
| 12 | 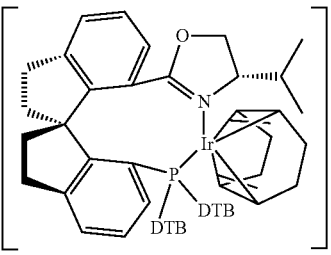 | sodium carbonate (0.25 mmol) | methanol | 100% | 98% |
| 13 | 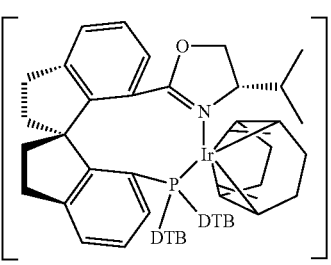 | cesium carbonate (025 mmol) | methanol | 100% | >99% |
| 14 | 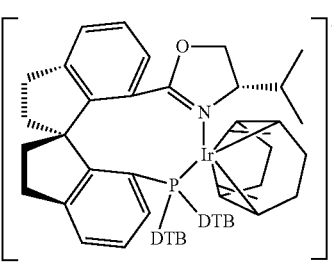 | cesium carbonate (0.25 mmol) | ethanol | 90% | 98% |
| 15 | 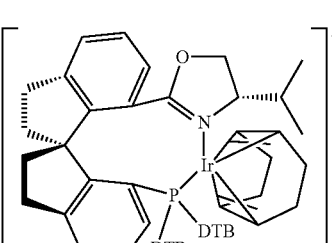 | cesium carbonate (0.25 mmol) | isopropanol | 80% | 98% |

Embodiment 4

Asymmetric Catalytic Hydrogenation of Tiglic Acid Derivatives

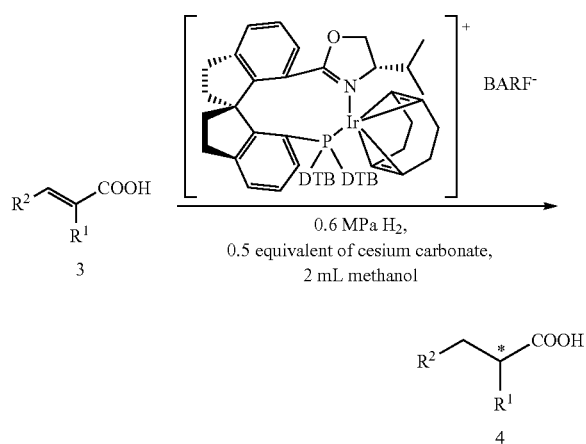

In the glove box, the catalyst

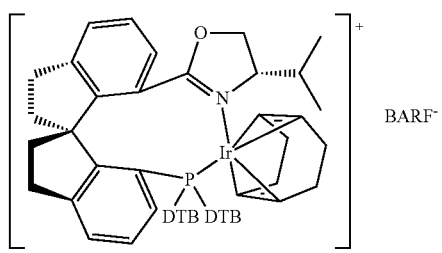

(2.4 mg, 0.00125 mmol), the substrate 3 (0.5 mmol) and cesium carbonate (82 mg, 0.25 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product is obtained. The conversion rate is analyzed through $^1$H NMR, after it is converted to amide, its ee value is analyzed through the chiral HPLC or SFC analysis. The experimental results obtained are shown in Table 4:

TABLE 4 the experimental results of asymmetric catalytic hydrogenation of tiglic acid derivatives

| | $R^1$ | $R^2$ | Conversion rate | Yield | ee value |
|---|---|---|---|---|---|
| 1 | Me | Me | 100% | 92% | 99.1% |
| 2 | Me | Et | 100% | 93% | 98% |
| 3 | Me | $^n$Pr | 100% | 89% | 99% |
| 4 | Me | $^i$Bu | 100% | 97% | 90% |
| 5 | Et | $^n$Pr | 100% | 89% | 99.4% |
| 6 | $^n$Pr | Me | 100% | 92% | 98% |

Embodiment 5

Asymmetric Catalytic Hydrogenation of (E)-2-[3-(3-methoxy-propoxy)-4-methoxy phenyl methylene]-3-methyl-butyric Acid

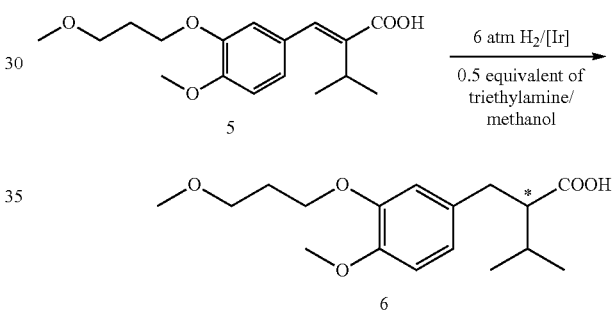

In the glove box, the catalyst (0.0025 mmol) and (E)-2-[3-(3-methoxy-propoxy)-4-methoxy phenyl methylene]-3-methyl-butyric acid 5 (77.1 mg, 0.25 mmol) are weighted in the reaction inner tube with stirring bar, then the reaction inner tube is sealed for use. When the reaction inner tube is took out, triethylamine (12.6 mg, 0.125 mmol) and anhydrous methanol (2 mL) are added with a syringe, then the inner tube is placed into the hydrogenation reactor, the mixture is stirred at the room temperature under the hydrogen pressure of 0.6 MPa for 24 h. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 6 is obtained. The conversion rate is analyzed through $^1$H NMR, after it is converted to amide, its ee value is analyzed through the chiral HPLC or SFC analysis. The experimental results obtained are shown in Table 5:

TABLE 5
the experimental results of asymmetric catalytic hydrogenation of (E)-2-[3-(3-methoxy-propoxy)-4-methoxy phenyl methylene]-3-methyl-butyric acid
| | Catalyst | | Conversion rate | Yield | ee value |
|---|---|---|---|---|---|
| 1 | 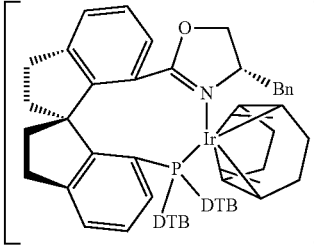 | BARF⁻ | 100% | 94% | 98% |
| 2 | 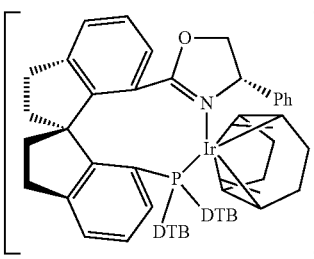 | BARF⁻ | 80% | 70% | 95% |
| 3 | 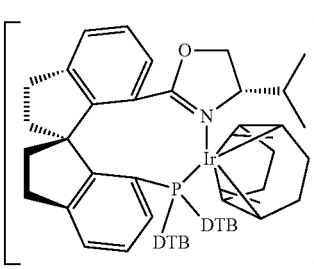 | BARF⁻ | 100% | 93% | 98% |
| 4 | 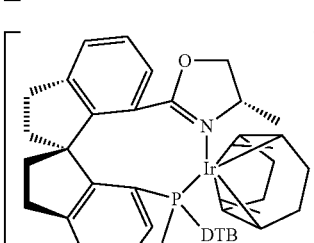 | BARF⁻ | 100% | 95% | 98% |
| 5 | 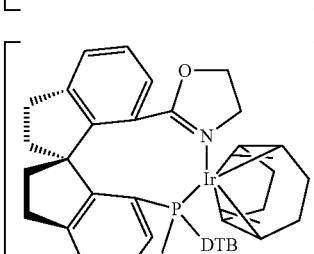 | BARF⁻ | 100% | 95% | 98% |
| 6 | 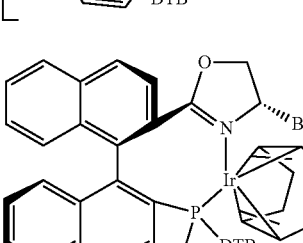 | BARF⁻ | 9% | — | — |

TABLE 5-continued the experimental results of asymmetric catalytic hydrogenation of (E)-2-[3-(3-methoxy-propoxy)-4-methoxy phenyl methylene]-3-methyl-butyric acid

| | Catalyst | Conversion rate | Yield | ee value |
|---|---|---|---|---|
| 7 | 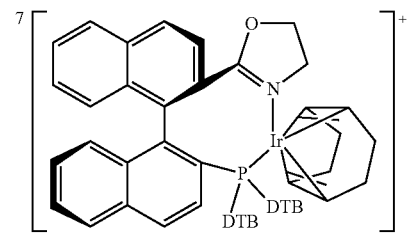 | 48% | 30% | 91% |

Embodiment 6

Asymmetric Catalytic Hydrogenation of (R)-2-[3-(3-methoxy-propoxy)-4-methoxy phenyl methylene]-3-methyl-butyric Acid

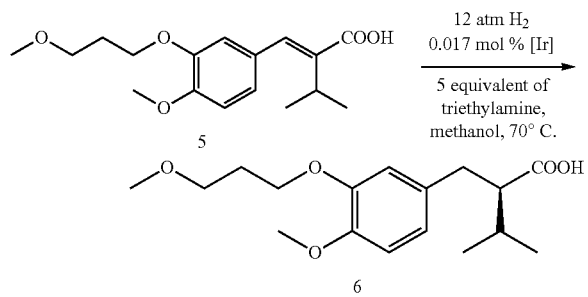

In the glove box, the catalyst

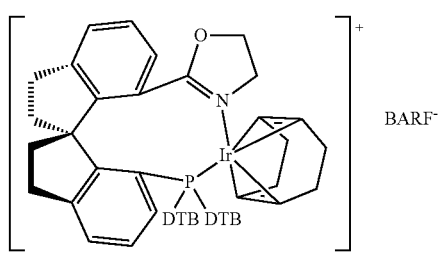

(0.8 mg, 0.417 μmol) and (E)-2-[3-(3-methoxy-propoxy)-4-methoxy phenyl methylene]-3-methyl-butyric acid 5 (771 mg, 2.5 mmol) are weighted in the reaction inner tube with stirring bar, then the reaction inner tube is sealed for use. When the reaction inner tube is took out, triethylamine (1.26 g, 12.5 mmol) and anhydrous methanol (3.5 mL) are added with a syringe, then the inner tube is placed into the hydrogenation reactor, the mixture is stirred in 70° C. oil bath under the hydrogen pressure of 1.2 MPa for 7 h. Then the stirring is stopped, the hydrogen is released. After the system is condensed by evaporating off rotatably, the system is adjusted pH<3 with 3N hydrochloric acid water solution, extracted with diethyl ether (50 mL×3), and separated, the organic phase is collected, washed with saturated salt water, and dried with anhydrous sodium sulfate. The desiccant is removed by suction filtration, the solvent is evaporated off by rotating, then the object product (R)-6 is obtained, and is a white solid, through the $^1$H NMR analysis, the conversion rate is 100% and the yield is 96%. Mp 44-45° C.; $[\alpha]_D^{21}$÷42.2 (c 1.0, CH$_2$Cl$_2$); $^1$H NMR (400 MHz, CDCl$_3$): δ 9.71 (brs, 1H, COOH), 6.73-6.68 (m, 3H, Ar—H), 4.06 (t, J=6.4 Hz, 2H, CH$_2$), 3.79 (s, 3H, CH$_3$), 3.53 (t, J=6.4 Hz, 2H, CH$_2$), 3.32 (s, 3H, CH$_3$), 2.81-2.71 (m, 2H, CH$_2$ and CH), 2.43-2.38 (m, 1H, CH$_2$), 2.08-2.01 (m, 2H, CH$_2$), 1.90 (sextet, J=6.4 Hz, 1H, CH), 1.00 (dd, J=13.2 and 6.8 Hz, 6H, CH$_3$); after it is converted to methyl ester, its ee value is 98% through the chiral SFC analysis. Under the same condition, the amount of the catalyst is further reduced to 0.01 mol %, the reaction lasts for 18 h, then the conversion rate is 97%, the yield is 95%, and the ee value is 95%.

Embodiment 7

Asymmetric Catalytic Hydrogenation of α-methoxy Cinnamic Acid

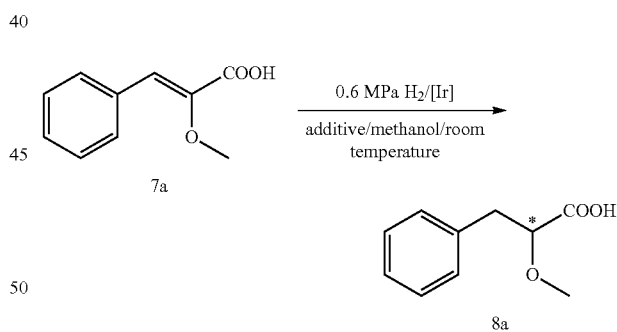

In the glove box, the catalyst (0.00125 mmol) and α-methoxy cinnamic acid 7a (89 mg, 0.5 mmol) are weighted in the reaction inner tube with stirring bar, then the reaction inner tube is sealed for use. When the reaction inner tube is took out, the additive and the solvent (2 mL) are added with a syringe, then the inner tube is placed into the hydrogenation reactor, the mixture is stirred at the room temperature under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 8a is obtained. The conversion rate is analyzed through ¹H NMR, after it is converted to amide, its ee value is analyzed through the chiral HPLC or SFC analysis. The experimental results obtained are shown in Table 6:

TABLE 6 the experimental results of asymmetric catalytic hydrogenation of α-methoxy cinnamic acid

| | Catalyst | Additive | Conversion rate | ee value |
|---|---|---|---|---|
| 1 | 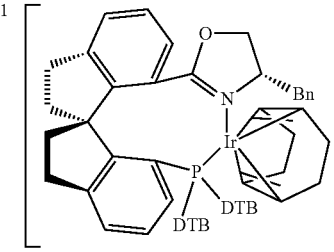 | triethylamine (0.25 mmol) | 95% | 99.5% |
| 2 | 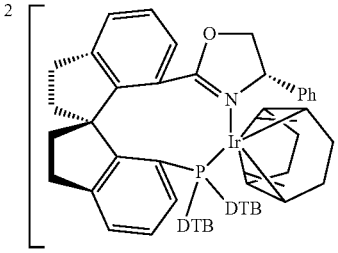 | triethylamine (0.25 mmol) | 90% | 99.8% |
| 3 | 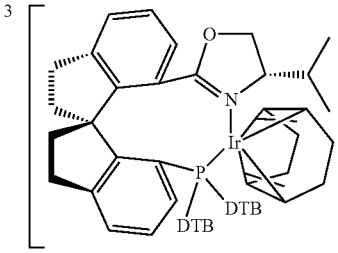 | triethylamine (0.25 mmol) | 95% | 99.5% |
| 4 | 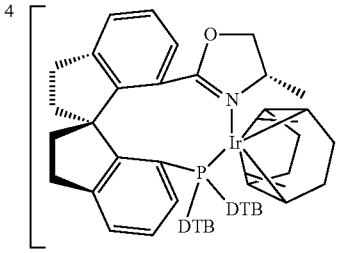 | triethylamine (0.25 mmol) | 95% | 99.5% |
| 5 | 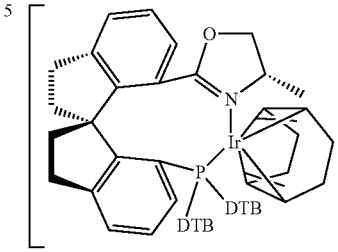 | cesium carbonate (0.25 mmol) | 100% | 99.3% |

Embodiment 8

Asymmetric Catalytic Hydrogenation of α-methoxy Cinnamic Acid Derivatives

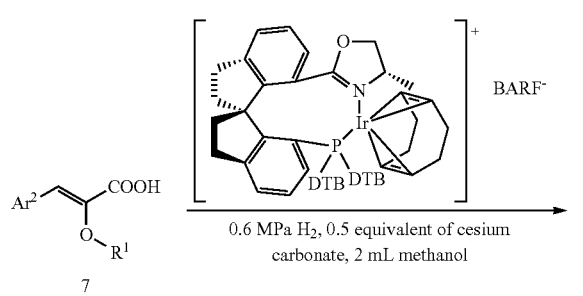

0.6 MPa H₂, 0.5 equivalent of cesium carbonate, 2 mL methanol

In the glove box, the catalyst (2.4 mg, 0.00125 mmol), the reaction substrate 7 (0.5 mmol) and cesium carbonate (82 mg, 0.25 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred at the room temperature under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 8 is obtained. The conversion rate is analyzed through $^1$H NMR, after it is converted to amide, its ee value is analyzed through the chiral SFC analysis. The experimental results obtained are shown in Table 7:

TABLE 7 the experimental results of asymmetric catalytic hydrogenation of α- methoxy cinnamic acid derivatives

|    | R¹ | Ar² | Conversion rate | Yield | ee value |
|----|----|----|---|---|---|
| 1  | Me | Ph | 100% | 95% | 99.3% |
| 2  | Me | o-Tol | 100% | 93% | 99.7% |
| 3  | Me | m-Tol | 100% | 91% | 99.0% |
| 4  | Me | p-Tol | 100% | 94% | 99.6% |
| 5  | Me | o-MeOPh | 100% | 97% | 99.2% |
| 6  | Me | m-MeOPh | 100% | 91% | 99.7% |
| 7  | Me | p-MeOPh | 100% | 92% | 99.7% |
| 8  | Me | o-ClPh | 100% | 95% | 99.4% |
| 9  | Me | m-ClPh | 100% | 93% | 99.3% |
| 10 | Me | p-ClPh | 100% | 91% | 99.8% |
| 11 | Me | o-BrPh | 100% | 91% | 99.5% |
| 12 | Me | m-BrPh | 100% | 94% | 99.6% |
| 13 | Me | p-NO₂Ph | 100% | 96% | 99.7% |
| 14 | Me | p-CF₃Ph | 100% | 95% | 99.2% |
| 15 | Me | 2-naphthyl | 100% | 93% | 99.8% |
| 16 | Et | Ph | 100% | 92% | 99.7% |
| 17 | Et | p-BnOPh | 100% | 93% | 99.5% |
| 18 | Bn | Ph | 100% | 94% | 99.5% |
| 19 | Bn | o-Tol | 100% | 93% | 99.8% |
| 20 | Bn | m-Tol | 100% | 94% | 99.8% |
| 21 | Bn | p-Tol | 100% | 91% | 99.8% |
| 22 | Bn | o-MeOPh | 100% | 93% | 99.4% |
| 23 | Bn | m-MeOPh | 100% | 95% | 99.4% |
| 24 | Bn | p-MeOPh | 100% | 93% | 99.6% |

Embodiment 9

Asymmetric Catalytic Hydrogenation of α-phenoxy-2-butenoic Acid

In the glove box, the catalyst (0.0025 mmol) and α-phenoxy-2-butenoic acid 9a (89 mg, 0.5 mmol) are weighted in the reaction inner tube with stirring bar, then the reaction inner tube is sealed for use. When the reaction inner tube is took out, the additive and the solvent (2 mL) are added with a syringe, then the inner tube is placed into the hydrogenation reactor, the mixture is stirred under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 10a is obtained. The conversion rate is analyzed through $^1$H NMR, after it is converted to amide, its ee value is analyzed through the chiral HPLC or SFC analysis. The experimental results obtained are shown in Table 8:

TABLE 8 the experimental results of asymmetric catalytic hydrogenation of α-phenoxy-2-butenoic acid

| | Catalyst | Additive | Solvent | Temperature | Conversion rate | ee value |
|---|---|---|---|---|---|---|
| 1 | 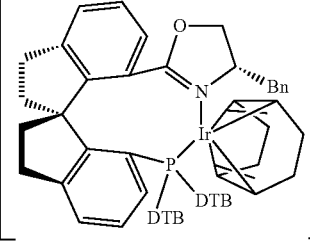 BARF⁻ | triethylamine (0.25 mmol) | methanol | room temperature | 32% | 98% |
| 2 | 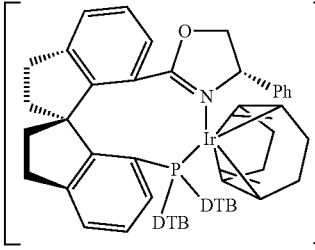 BARF⁻ | triethylamine (0.25 mmol) | methanol | room temperature | 22% | 90% |
| 3 | 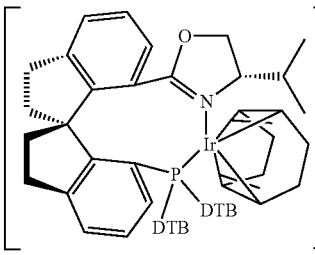 BARF⁻ | triethylamine (0.25 mmol) | methanol | room temperature | 26% | 99% |
| 4 | 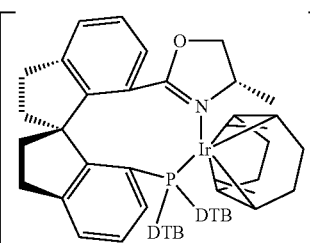 BARF⁻ | triethylamine (0.25 mmol) | methanol | room temperature | 28% | 98% |
| 5 | 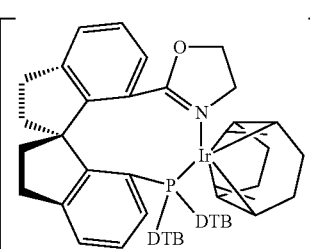 BARF⁻ | triethylamine (0.25 mmol) | methanol | room temperature | 10% | 95% |

TABLE 8-continued the experimental results of asymmetric catalytic hydrogenation of α-phenoxy-2-butenoic acid

| | Catalyst | Additive | Solvent | Temperature | Conversion rate | ee value |
|---|---|---|---|---|---|---|
| 6 | 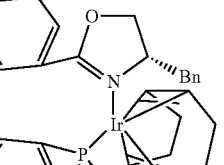 | cesium carbonate (0.25 mmol) | methanol | room temperature | 93% | 98% |
| 7 | 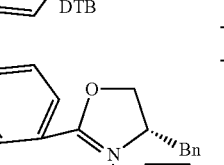 | cesium carbonate (0.25 mmol) | ethanol | room temperature | 95% | 98% |
| 8 | 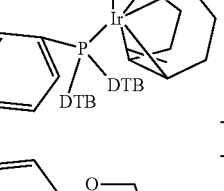 | cesium carbonate (0.25 mmol) | isopropanol | room temperature | 56% | 98% |
| 9 | 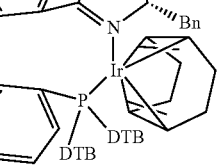 | cesium carbonate (0.25 mmol) | methanol | 40° C. | 100% | 99% |

Embodiment 10

Asymmetric Catalytic Hydrogenation of α-phenoxy-2-butenoic Acid Derivatives

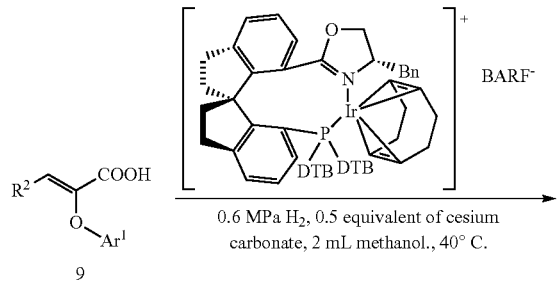

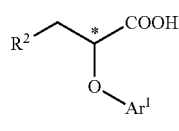

In the glove box, the catalyst

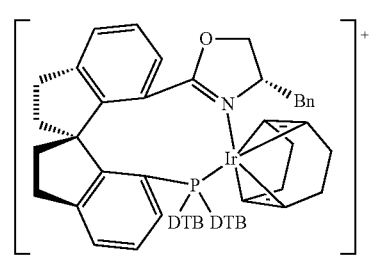

(4.8 mg, 0.0025 mmol), the reaction substrate 9 (0.5 mmol) and cesium carbonate (82 mg, 0.25 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred in 40° C. water bath under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 10 is obtained. The conversion rate is analyzed through $^1$H NMR, after it is converted to amide, its ee value is analyzed through the chiral HPLC or SFC analysis. The experimental results obtained are shown in Table 9:

TABLE 9 the experimental results of asymmetric catalytic hydrogenation of α- phenoxy -2- butenoic acid derivatives

|   | Ar$^1$ | R$^2$ | Conversion rate | Yield | ee value |
|---|--------|-------|-----------------|-------|----------|
| 1 | Ph | Me | 100% | 95% | 99% |
| 2 | m-Tol | Me | 100% | 93% | 98% |
| 3 | m-BrPh | Me | 100% | 91% | 96% |
| 4 | p-Tol | Me | 100% | 92% | >99% |
| 5 | p-$^t$BuPh | Me | 100% | 94% | 97% |
| 6 | p-MeOPh | Me | 100% | 93% | >99% |
| 7 | p-ClPh | Me | 100% | 92% | 98% |
| 8 | p-BrPh | Me | 100% | 93% | 97% |
| 9 | 3,5-F$_2$Ph | Me | 100% | 88% | 89% |
| 10 | 2-naphthyl | Me | 100% | 94% | 97% |

Embodiment 11

Asymmetric Catalytic Hydrogenation of α-phenoxy Cinnamic Acid and Derivatives Thereof

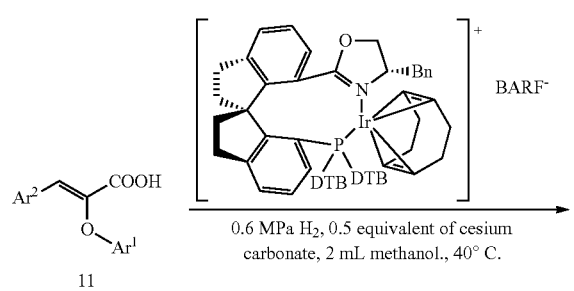

0.6 MPa H$_2$, 0.5 equivalent of cesium carbonate, 2 mL methanol., 40° C.

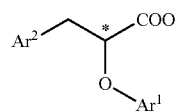

In the glove box, the catalyst

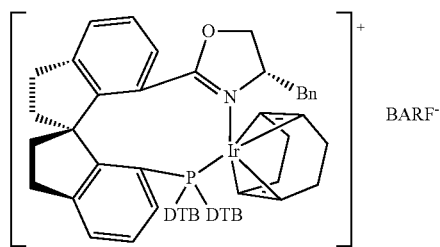

(4.8 mg, 0.0025 mmol), the reaction substrate 11 (0.5 mmol) and cesium carbonate (82 mg, 0.25 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred in 40° C. water bath under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 12 is obtained. The conversion rate is analyzed through $^1$H NMR, after it is converted to amide, its ee value is analyzed through the chiral HPLC or SFC analysis. The experimental results obtained are shown in Table 10:

TABLE 10 the experimental results of asymmetric catalytic hydrogenation of α- phenoxy cinnamic acid and derivatives thereof

|    | Ar$^1$ | Ar$^2$ | Conversion rate | Yield | ee value |
|----|--------|--------|-----------------|-------|----------|
| 1 | Ph | Ph | 100% | 95% | 99.6% |
| 2 | Ph | m-Tol | 100% | 91% | 99.7% |
| 3 | Ph | p-Tol | 100% | 94% | 99.8% |
| 4 | Ph | o-MeOPh | 100% | 98% | 97% |
| 5 | Ph | m-MeOPh | 100% | 96% | 99.6% |
| 6 | Ph | p-MeOPh | 100% | 91% | 99.4% |
| 7 | Ph | m-ClPh | 100% | 90% | 99.8% |
| 8 | Ph | p-ClPh | 100% | 87% | 99.7% |
| 9 | Ph | p-FPh | 100% | 93% | 99% |
| 10 | Ph | o-CF$_3$Ph | 100% | 91% | 99.8% |
| 11 | Ph | m-CF$_3$Ph | 100% | 92% | 99.7% |
| 12 | Ph | p-CF$_3$Ph | 100% | 93% | 99% |
| 13 | Ph | 1-naphthyl | 100% | 98% | 99.4% |
| 14 | Ph | 2-naphthyl | 100% | 92% | 99.2% |
| 15 | Ph | furyl | 100% | 94% | 99% |
| 16 | o-Tol | Ph | 100% | 89% | 99.5% |
| 17 | m-Tol | Ph | 100% | 92% | 99.5% |
| 18 | p-Tol | Ph | 100% | 91% | 99.5% |
| 19 | p-MeOPh | Ph | 100% | 94% | 99.8% |
| 20 | p-ClPh | Ph | 100% | 93% | 99.1% |

Embodiment 12

Asymmetric Catalytic Hydrogenation of α-phenyl Cinnamic Acid

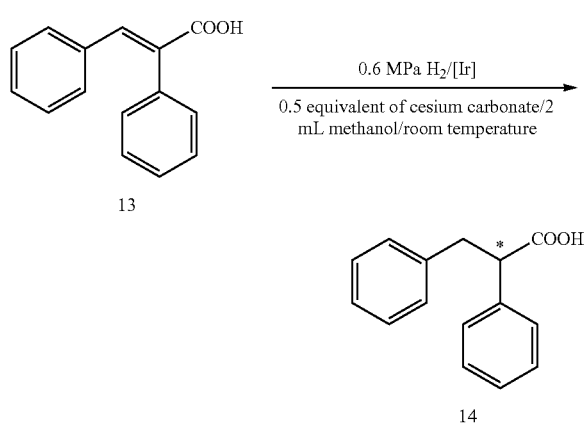

In the glove box, the catalyst (0.0025 mmol), α-phenyl cinnamic acid 13 (56 mg, 0.25 mmol) and cesium carbonate (41 mg, 0.125 mmol) are weighted in the reaction inner tube with stirring bar, then the reaction inner tube is sealed for use. When the reaction inner tube is took out, anhydrous methanol (2 mL) is added with a syringe, then the inner tube is placed into the hydrogenation reactor, the mixture is stirred at the room temperature under the hydrogen pressure of 0.6 MPa till the pressure stops declining. Then the stirring is stopped, the hydrogen is released. After the system is condensed by evaporating off rotatably, the system is adjusted pH<3 with 3N hydrochloric acid water solution, extracted with diethyl ether (10 mL×3), and separated, the organic phase is collected, washed with saturated salt water, and dried with anhydrous sodium sulfate. The desiccant is removed by suction filtration, the solvent is evaporated off by rotating, then the object product 14 is obtained. The conversion rate is analyzed through $^1$H NMR, after it is converted to amide, its ee value is analyzed through the chiral HPLC or SFC analysis. The experimental results obtained are shown in Table 11:

TABLE 11 the experimental results of asymmetric catalytic hydrogenation of α-phenyl cinnamic acid

| Catalyst | Conversion rate | ee value |
|---|---|---|
| 1 [structure] BARF⁻ | 100% | 91% |
| 2 [structure] BARF⁻ | 100% | 93% |

We claim:

1. A preparation method of chiral carboxylic acids, being that the asymmetric catalytic hydrogenation of tri-substituted α,β-unsaturated carboxylic acids is carried out with the presence of a chiral iridium complex of a chiral phosphor nitrogen ligand and an alkaline additive to obtain chiral carboxylic acids having optical purity, wherein it is carried out by the following catalytic hydrogenation reaction process:

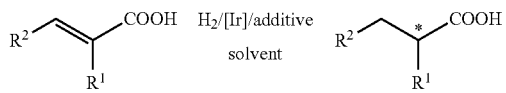

wherein: [Ir] is the iridium complex catalyst of the chiral phosphor nitrogen ligand; $R^1$ is $C_1$-$C_8$ alkyl, $R^2$ is $C_1$-$C_8$ alkyl, $C_1$-$C_8$ alkyl-substituted phenoxy, $C_1$-$C_8$ alkoxy-substituted phenoxy, halogenated phenyl, or naphthyl, furyl, wherein the iridium complex catalyst of the chiral phosphor nitrogen ligand has the following structural formula:

[structure] X wherein:

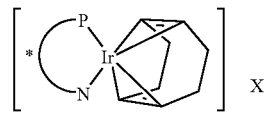

is the chiral phosphor nitrogen ligand;

[structure]

is cyclooctadiene; X is halogen, $C_1$-$C_8$ carboxylate radical, sulfate radical, tetra (3,5-bis trifluoromethylphenyl) borate radical, tetra (pentafluorophenyl) borate radical, tetra (perfluoro-tert-butoxy) aluminum ion, tetra (hexafluoroisopropoxy) aluminum ion, hexafluoro phosphate ion, hexafluoro antimonlate ion, tetrafluoro borate ion or triflluoro methanesulfonate ion; cyclooctadiene ligand can be substituted by ethylene or norbornadiene wherein the chiral phosphor nitrogen ligand contained in the iridium complex catalyst of the chiral phosphor nitrogen ligand has the following structural formula:

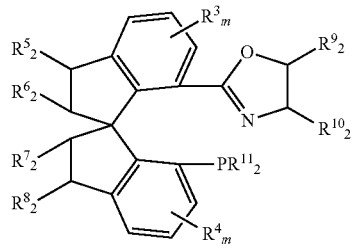

wherein: m=0-3, each of $R^3$, $R^4$, $R^5$, $R^6$, $R^7$, $R^8$, and $R^9$ are H;

$R^{10}$ is H, $C_1$-$C_8$ alkyl, benzyl, or phenyl;

$R^{11}$ is $C_1$-$C_8$ alkyl, phenyl, $C_1$-$C_8$ alkyl-substituted phenyl, or $C_1$-$C_8$ alkoxy-substituted phenyl;

the $C_1$-$C_8$ alkyl is methyl, ethyl, n-propyl, isopropyl, cyclopropyl, n-butyl, isobutyl, sec-butyl, tert-butyl, cyclobutyl, pentyl, isoamyl, neopentyl, sec-pentyl, tert pentyl, cyclopentyl, n-hexyl, isohexyl, neohexyl, sec-hexyl, tert-hexyl, cyclohexyl, n-heptyl, isoheptyl, neoheptyl, sec-heptyl, tert-heptyl, cycloheptyl, n-octyl, isooctyl, neooctyl, sec-octyl, tert-octyl or cyclooctyl;

the $C_1$-$C_8$ alkoxy is methoxy, ethoxy, n-propoxy, isopropoxy, cyclopropoxy, n-butoxy, isobutoxy, sec-butoxy, tert-butoxy, cyclobutoxy, n-pentyloxy, isopentyloxy, neopentyloxy, sec-pentyloxy, tert-pentyloxy, cyclopentyloxy, n-hexyloxy, isohexyloxy, neohexyloxy, sec-hexyloxy, tert-hexyloxy, cyclohexyloxy, n-heptyloxy, isoheptyloxy, neoheptyloxy, sec-heptyloxy, tert-heptyloxy, cycloheptyloxy, n-octyloxy, iso-octyloxy, neooctyloxy, sec-octyloxy, tert-octyloxy, or cyclooctyloxy.

2. The preparation method of chiral carboxylic acids according to claim 1, wherein under the protection of argon or nitrogen, the catalyst and the substrate are added into the inner tube of the reactor, then the additive and the solvent are added, the reactor is sealed and the air in the reactor is replaced carefully with hydrogen for 3 to 5 times, after the reactor is filled with hydrogen to the desired pressure, the mixture is stirred to the end;

the catalytic hydrogenation reaction condition is that: the solvent used is ethyl acetate or $C_1$-$C_6$ alcohol; the amount of the catalyst is 0.001-1 mol %; the concentration of the substrate is 0.001~10.0 M; the additive is one or several of iodine, isopropylamine, tert-butylamine, dimethylamine, diethyl amine, diisopropylamine, diisopropyl ethylamine, trimethylamine, triethylamine, 1,8-diazabicyclo[5,4,0]undec-7-ene (DBU), 1,4-diazabicyclo[2,2,2]octane (DABCO), sodium hydride, sodium hydroxide, sodium carbonate, sodium bicarbonate, sodium tert-butyl alcohol, potassium hydroxide, potassium carbonate, potassium bicarbonate, potassium tert-butyl alcohol, cesium hydroxide, cesium carbonate; the reaction temperature is 0-100° C. the hydrogen pressure is 0.1-10 MPa; the tri-substituted α,β-unsaturated carboxylic acid is stirred in the reactor to react for 0.5-48 h.

3. The preparation method of chiral carboxylic acids according to claim 2, wherein the solvent is ethyl acetate, methanol, ethanol or isopropanol.

4. The preparation method of chiral carboxylic acids according to claim 2, wherein the additive is diisopropylamine, diisopropyl ethylamine, triethylamine, sodium carbonate, sodium bicarbonate, potassium hydroxide, potassium carbonate, potassium bicarbonate, cesium carbonate.

5. The preparation method of chiral carboxylic acids according to claim 1, wherein under the optimal hydrogenation reaction condition, the optical purity of the chiral carboxylic acids is at least 90% ee.

6. The preparation method of chiral carboxylic acids according to claim 1, wherein the iridium complex catalyst of the chiral phosphor nitrogen ligand has the following structural formula:

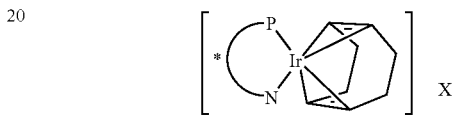

Wherein:

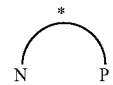

is the chiral phosphor nitrogen ligand;

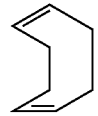

is cyclooctadiene; X is halogen, $C_1$-$C_8$ carboxylate radical, sulfate radical, tetra (3,5-bis trifluoromethylphenyl) borate radical, tetra (pentafluorophenyl) borate radical, tetra (perfluoro-tert-butoxy) aluminum ion, tetra (hexafluoroisopropoxy) aluminum ion, hexafluoro phosphate ion, hexafluoro antimonlate ion, tetrafluoro borate ion or triflluoro methanesulfonate ion; cyclooctadiene ligand can be substituted by ethylene or norbornadiene, wherein the chiral phosphor nitrogen ligand contained in the iridium complex catalyst of the chiral phosphor nitrogen ligand has the following structural formula:

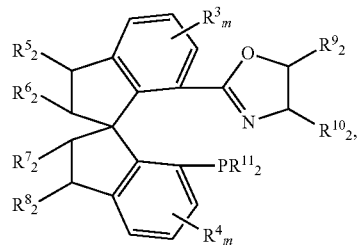

wherein: m=0-3; each of $R^3$, $R^4$, $R^5$, $R^6$, $R^7$, $R^8$, and $R^9$ are H;

$R^{10}$ is H, $C_1$-$C_8$ alkyl, benzyl, or phenyl;

$R^{11}$ is $C_1$-$C_8$ alkyl, phenyl, $C_1$-$C_8$ alkyl-substituted phenyl, or $C_1$-$C_8$ alkoxy-substituted phenyl;

the $C_1$-$C_8$ alkyl is methyl, ethyl, n-propyl, isopropyl, cyclopropyl, n-butyl, isobutyl, sec-butyl, tert-butyl, cyclobutyl, pentyl, isoamyl, neopentyl, sec-pentyl, tert pentyl, cyclopentyl, n-hexyl, isohexyl, neohexyl, sec-hexyl, tert-hexyl, cyclohexyl, n-heptyl, isoheptyl, neoheptyl, sec-heptyl, tert-heptyl, cycloheptyl, n-octyl, isooctyl, neooctyl, sec-octyl, tert-octyl or cyclooctyl;

the $C_1$-$C_8$ alkoxy is methoxy, ethoxy, n-propoxy, isopropoxy, cyclopropoxy, n-butoxy, isobutoxy, sec-butoxy, tert-butoxy, cyclobutoxy, n-pentyloxy, isopentyloxy, neopentyloxy, sec-pentyloxy, tert-pentyloxy, cyclopentyloxy, n-hexyloxy, isohexyloxy, neohexyloxy, sec-hexyloxy, tert-hexyloxy, cyclohexyloxy, n-heptyloxy, isoheptyloxy, neoheptyloxy, sec-heptyloxy, tert-heptyloxy, cycloheptyloxy, n-octyloxy, iso-octyloxy, neooctyloxy, sec-octyloxy, tert-octyloxy, or cyclooctyloxy.

7. The preparation method of chiral carboxylic acids according to claim 1, wherein the tri-substituted α,β-unsaturated carboxylic acids are:

α-methyl cinnamic acid;

tiglic acid; or

α-phenyl cinnamic acid.

* * * * *